United States Patent
Hong et al.

(10) Patent No.: US 10,265,276 B2
(45) Date of Patent: *Apr. 23, 2019

(54) PHARMACEUTICAL COMPOSITION FOR PREVENTING OR TREATING ARTHRITIS OR INFLAMMATORY DISEASE CONTAINING 2-METHOXY-4-(3-(4-METHOXYPHENYL) PROPYL-1-EN-1-YL)PHENOL AS ACTIVE INGREDIENT

(71) Applicant: CHUNGBUK NATIONAL UNIVERSITY INDUSTRY-ACADEMIC COOPERATION FOUNDATION, Cheongju-si, Chungcheongbuk-do (KR)

(72) Inventors: Jin Tae Hong, Cheongju-si (KR); Hee Pom Lee, Cheongju-si (KR); Young Wan Ham, Orem, UT (US); Chun Sik Kim, Cheongju-si (KR); Heon Sang Jung, Cheongju-si (KR); Dae Hwan Kim, Cheongju-si (KR)

(73) Assignee: CHUNGBUK NATIONAL UNIVERSITY INDUSTRY-ACADEMIC COOPERATION FOUNDATION, Chungcheongbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/564,850
(22) PCT Filed: Apr. 8, 2016
(86) PCT No.: PCT/KR2016/003728
§ 371 (c)(1),
(2) Date: Oct. 6, 2017
(87) PCT Pub. No.: WO2016/163818
PCT Pub. Date: Oct. 13, 2016

(65) Prior Publication Data
US 2018/0133169 A1    May 17, 2018

(30) Foreign Application Priority Data
Apr. 9, 2015  (KR) .................. 10-2015-0050411

(51) Int. Cl.
*A61K 31/075* (2006.01)
*A61K 31/05* (2006.01)
(Continued)

(52) U.S. Cl.
CPC ............ *A61K 31/05* (2013.01); *A61K 9/0019* (2013.01); *A61K 9/2018* (2013.01);
(Continued)

(58) Field of Classification Search
CPC .................................................. A61K 31/09
(Continued)

(56) References Cited

U.S. PATENT DOCUMENTS 7,598,294 B2   10/2009   Potter et al.
2004/0254149 A1   12/2004   Potter et al.
(Continued)

FOREIGN PATENT DOCUMENTS

KR   1020080030938 A   7/2010
KR      101126164 B1   3/2012
(Continued)

OTHER PUBLICATIONS

Ban, et al., "Anti-arthritis effects of (E)-2,4-bis(p-hydroxyphenyl)-2-butenal are mediated by inhibition of the STAT3 pathway", *Br J Pharmacol.* Jun. 2014;171(11):2900-12.
(Continued)

*Primary Examiner* — Shengjun Wang
(74) *Attorney, Agent, or Firm* — DLA Piper LLP (US)

(57) ABSTRACT

Disclosed herein is a pharmaceutical composition for treating or preventing inflammatory diseases or arthritis, which includes 2-methoxy-4-(3-(4-methoxyphenyl)prop-1-en-1-
(Continued)

yl)phenol or a pharmaceutically acceptable salt thereof as an active ingredient. The pharmaceutical composition exhibits superior therapeutic efficacy against arthritis without any side effects such as toxicity, etc.

6 Claims, 12 Drawing Sheets

(51) Int. Cl.

| | |
|---|---|
| *A61K 31/045* | (2006.01) |
| *A61P 19/02* | (2006.01) |
| *A61P 29/00* | (2006.01) |
| *A61K 9/00* | (2006.01) |
| *A61K 9/20* | (2006.01) |
| *A61K 9/48* | (2006.01) |

(52) U.S. Cl.
CPC .......... *A61K 9/4858* (2013.01); *A61K 31/045* (2013.01); *A61P 19/02* (2018.01); *A61P 29/00* (2018.01)

(58) Field of Classification Search
USPC .................................................. 514/720, 721
See application file for complete search history.

(56) References Cited

U.S. PATENT DOCUMENTS

| | | |
|---|---|---|
| 2005/0260290 A1 | 11/2005 | Raskin et al. |
| 2010/0028262 A1 | 2/2010 | Potter et al. |

FOREIGN PATENT DOCUMENTS

| | | |
|---|---|---|
| KR | 20120094308 | 8/2012 |
| KR | 101201549 | 11/2012 |
| KR | 20140093435 | 7/2014 |
| KR | 1020140045894 | 11/2016 |

OTHER PUBLICATIONS

Boyle, et al., "The JAK inhibitor tofacitinib suppresses synovial JAK1-STAT signalling in rheumatoid arthritis", Ann Rhem Dis 2015, 74: 1311-1316.

Cai, et al., "Pathways by which interleukin 17 induces articular cartilage breakdown in vitro and in vivo", *Cytokine*. Oct. 7, 2001;16(1):10-21.

International Search Report issued in PCT/KR2016/003728 dated Jun. 27, 2016.

Jhun, et al., "Red ginseng extract ameliorates autoimmune arthritis via regulation of STAT3 pathway, Th17/Treg balance, and osteoclastogenesis in mice and human", Mediators Inflamm. 2014;2014:351856.

Lee, et al., "Interleukin-17 increases the expression of Toll-like receptor 3 via the STAT3 pathway in rheumatoid arthritis fibroblast-like synoviocytes", *Immunology*. Mar. 2014;141(3):353-61.

Park, et al., "JAK2-STAT3 blockade by AG490 suppresses autoimmune arthritis in mice via reciprocal regulation of regulatory T Cells and Th17 cells", *J Immunol*. May 1, 2014;192(9):4417-24.

Pathak, et al., "Syntheses of 2-methoxyestradiol and eugenol template based diarylpropenes as non-steroidal anticancer agents", RCS Adv. 2014 (4): 35171-35185.

Ryu, et al., "Treatment of IL-21R-Fc control autoimmune arthritis via suppression of STAT3 signal pathway mediated regulation of the Th17/Treg balance and plasma B cells", *Immunol Lett*. Feb. 2015;163(2):143-50.

Wu, et al., "Evaluation and discovery of novel synthetic chalcone derivatives as anti-inflammatory agents", *J Med Chem*. Dec. 8, 2011;54(23):8110-23.

Yang, et al., "EGCG Attenuates Autoimmune Arthritis by Inhibition of STAT3 and HIF-1α with Th17/Treg Control", PLoS One 2014, 9(2): 1-11.

PHARMACEUTICAL COMPOSITION FOR PREVENTING OR TREATING ARTHRITIS OR INFLAMMATORY DISEASE CONTAINING 2-METHOXY-4-(3-(4-METHOXYPHENYL)PROPYL-1-EN-1-YL)PHENOL AS ACTIVE INGREDIENT

CROSS-REFERENCE TO RELATED APPLICATIONS

The present application is the 35 U.S.C. § 371 National Stage Application of PCT/KR2016/003728, filed Apr. 8, 2016, which claims priority to and the benefit of Korean Patent Application No. 10-2015-0050411, filed on Apr. 9, 2015, the disclosures of which are incorporated herein by reference in their entirety.

FIELD OF INVENTION

The present invention relates to a pharmaceutical composition for treating or preventing inflammatory diseases or arthritis, which includes 2-methoxy-4-(3-(4-methoxyphenyl)prop-1-en-1-yl)phenol having a novel structure.

BACKGROUND

Inflammation refers to a condition in which a series of complex physiological reactions such as activation of enzymes by various inflammatory mediators and immune cells, secretion of inflammatory mediators, body fluid infiltration, cell migration, tissue destruction, and the like occur when tissues are stimulated by damage or exogenous sources of infection, such as bacteria, fungi, viruses, etc., and thus is accompanied with symptoms such as erythema, edema, pyrexia, pain, etc.

As described above, an in vivo defense response for restoring the structure and function of the tissues damaged by infection, trauma, etc. is generally referred to as an inflammatory response.

Migration of white blood cells into a site of inflammation is important for providing a swift solution to the infection and recovering from tissue damage caused by various traumas. However, an excessive or prolonged inflammatory response, which may be caused by unremoved exogenous sources of infection or endogenous substances, leads to damaged human tissues, and diseases as cancer, inflammatory skin disease, arthritis, etc.

The inflammatory diseases are classified into acute and chronic inflammatory diseases whose symptoms or pathological features are distinguishable. Local symptoms of acute inflammation such as allergies or bacterial and viral infections appear as changes in blood flow and blood vessel size, a change in vasopermeability, and leukocytic infiltration.

On the other hand, main pathological features of chronic inflammation, including rheumatoid arthritis, atherosclerosis, chronic nephritis, liver cirrhosis, etc., include prolonged infiltration of monocytes, neutrophils, lymphocytes, and plasma cells into sites of inflammation because inflammation inducers are not removed, leading to chronic inflammatory responses.

Various factors are associated with the inflammatory response in inflammatory diseases. Specifically, inflammatory mediators expressed in the site of inflammation include cytokines, chemokines, reactive oxygen intermediates, cycloxygenase-2 (COX-2), 5-lipoxygenase (5-LOX), matrix metalloproteinase (MMP), etc., and play an important role in occurrence and maintenance of the inflammatory response.

It has been known that expression of such inflammatory mediators is regulated by transcription factors, such as nuclear factor κB (NF-κB), signal transducer and activator of transcription 3 (STAT3), activator protein 1 (AP-1), hypoxia-inducible factor 1a (HIF-1a), etc.

For example, the present inventors have proposed that 2,4-bis(p-hydroxyphenyl)-2-butenal induces inactivation of NF-κB, and thus may be used as a medicine having an anti-inflammatory or anti-arthritic effect, as disclosed in Korean Unexamined Patent Publication No. 2012-0094308.

Also, Korean Unexamined Patent Publication No. 2014-0093435 discloses that chlorogenic acid derivatives suppress excessive nitric oxide generation, and thus may be used as therapeutic agents against inflammatory diseases, which have an effective anti-inflammatory activity.

Meanwhile, in addition to NF-κB, STAT3 is also an important transcription factor associated with inflammatory and immune responses.

As a representative inflammatory disease, arthritis can be treated and prevented by inhibiting the activity of STAT3.

Arthritis is a representative cartilage-related disorder that is generally referred to as a condition by what causes an inflammatory change occurring in the joints, and refers to a condition caused by the loss of cartilage serving to connect two bones so that the bones move smoothly.

Arthritis is divided into various types of arthritis such as degenerative arthritis or osteoarthritis, rheumatoid arthritis, avascular necrosis of the femoral head, traumatic arthritis, tuberculosis arthritis, and pyogenic arthritis. Currently, there are approximately one million arthritis patients in Korea. Here, women outnumber men two to one. In this case, arthritis is most often observed in climacteric women.

Among these, osteoarthritis (degenerative arthritis) is a type of arthritis that develops due to a degenerative change in cartilage and its surrounding bones among various components constituting the joint, that is, a joint disease which is generally severely painful in the joints under full body weight, that is, knee joints, hip joints, etc., makes it hard to move, and may lead to joint deformation when left untreated.

Osteoarthritis is a representative degenerative disease that is closely associated with aging and from which approximately 10 to 15% of the total population suffers. In particular, approximately 60 to 80% of the elderly population aged 65 or older suffers from osteoarthritis. The causes of osteoarthritis are deeply associated with senility or excess weight, and osteoarthritis develops more often and severely in women with age. Initial symptoms of osteoarthritis involve a throbbing pain in one or two joints with stiffness, and may lead to joint deformation when left untreated for a long time.

The therapeutic effects on arthritis associated with STAT3 are disclosed in various documents [Jun-Geol Ryu et al., Treatment of IL-21R-Fc control autoimmune arthritis via suppression of STAT3 signal pathway mediated regulation of the Th17/Treg balance and plasma B cells, *Immunol. Lett.* 2015, 163(2), 143-150; Boyle D L et al., The JAK inhibitor tofacitinib suppresses synovial JAK1-STAT signaling in rheumatoid arthritis, *Ann Rheum Dis.* 2014 Nov. 14; JooYeon Jhun et al., Red ginseng extract ameliorates autoimmune arthritis via regulation of STAT3 pathway, Th17/Treg balance, and osteoclastogenesis in mice and human, *Mediators Inflamm.* 2014; 2014:351856; Seon-Yeong Lee et al., Interleukin-17 increases the expression of Toll-like receptor 3 via the STAT3 pathway in rheumatoid arthritis fibroblast-like synoviocytes, *Immunology.* 141(3), 353-361;

Jin-Sil Park et al., JAK2-STAT3 blockade by AG490 suppresses autoimmune arthritis in mice via reciprocal regulation of regulatory T Cells and Th17 cells, *J. Immunol.* 2014, 192(9), 4417-4424; Eun-Ji Yang et al., EGCG attenuates autoimmune arthritis by inhibition of STAT3 and HIF-1α with Th17/Treg control. *PLoS One.* 2014, 9(2), e86062].

Typical methods of treating arthritis known in the art include drug therapies using painkillers, steroids, non-steroidal anti-inflammatory agents, etc., or using chondroprotective agents such as glucosamine, chondroitin, etc., surgical treatments such as artificial joint replacement surgery, etc. The drug therapies serve to non-specifically alleviate pain or reduce the inflammatory response itself, and the chondroprotective agents serve to minimize the loss of function of the joint by supplying nutrients to chondrocytes or reducing the impact on the joint. However, the therapy using drugs has a significant purpose of alleviating pain, but may have severe side effects caused by the use of drugs, such as dysfunction of various organs, depression, bacterial infections, etc.

Therefore, there is a need for sustainable development of effective methods of treating arthritis, which have few side effects but high safety. Also, as the aging of population proceeds rapidly with the recent entrance into an aging society, the market for arthritis therapeutic agents tends to constantly grow.

In the case of the arthritis therapeutic agents, research on new drug development has mainly featured the development of biological preparations so far. However, after a TNF-α inhibitor has been developed based on the mechanism of pathogenesis, remarkably high sales were achieved within a short period of time and a significant added value was created due to the breakthrough therapeutic effects.

For example, Korean Registered Patent No. 10-1126164 discloses that an essential oil extracted from *Curcuma wenyujin* is used as an active ingredient, has an anti-inflammatory activity because it serves to suppress TNF-α production, and may be used for compositions for preventing and treating inflammatory diseases such as arthritis.

Also, Korean Registered Patent No. 10-1201549 discloses that a pharmaceutical composition contains an extract of *Eucommia ulmoides* as an active ingredient, and thus may be used as a therapeutic agent for rheumatoid arthritis, which has an anti-inflammatory activity and an inhibitory effect on osteoclasts.

These patents exhibit high stability when administered as herbal preparations, but it is difficult to expect a fundamental therapeutic effect against arthritis.

PRIOR-ART DOCUMENTS

Patent Documents

Patent Document 1: Korean Unexamined Patent Publication No. 2012-0094308
Patent Document 2: Korean Unexamined Patent Publication No. 2014-0093435
Patent Document 3: Korean Registered Patent No. 10-1126164
Patent Document 4: Korean Registered Patent No. 10-1201549

Non-Patent Documents

Non-patent Document 1: Jianzhang Wu et al., Evaluation and Discovery of Novel Synthetic Chalcone Derivatives as Anti-Inflammatory Agents, J. Med. Chem. 2011, 54, 8110-8123
Non-patent Document 2: Liping Cai et al., PATHWAYS BY WHICH INTERLEUKIN 17 INDUCES ARTICULAR CARTILAGE BREAKDOWN IN VITRO AND IN VIVO, Cytokine. 2001, 16(1), 10-21
Non-patent Document 3: Jung Ok Ban et al., Anti-arthritis effects of (E)-2,4-bis(p-hydroxyphenyl)-2-butenal are mediated by inhibition of the STAT3 pathway, Br. J. Pharmacol. 2014, 171(11), 2900-2912
Non-patent Document 4: Jun-Geol Ryu et al., Treatment of IL-21R-Fc control autoimmune arthritis via suppression of STAT3 signal pathway-mediated regulation of the Th17/Treg balance and plasma B cells, Immunol. Lett. 2015, 163(2), 143-150
Non-patent Document 5: Boyle D L et al., The JAK inhibitor tofacitinib suppresses synovial JAK1-STAT signaling in rheumatoid arthritis, Ann Rheum Dis. 2014 Nov. 14
Non-patent Document 6: JooYeon Jhun et al., Red ginseng extract ameliorates autoimmune arthritis via regulation of STAT3 pathway, Th17/Treg balance, and osteoclastogenesis in mice and humans, Mediators Inflamm. 2014; 2014:351856
Non-patent Document 7: Seon-Yeong Lee et al., Interleukin-17 increases the expression of Toll-like receptor 3 via the STAT3 pathway in rheumatoid arthritis fibroblast-like synoviocytes, Immunology. 141(3), 353-361
Non-patent Document 8: Jin-Sil Park et al., JAK2-STAT3 blockade by AG490 suppresses autoimmune arthritis in mice via reciprocal regulation of regulatory T Cells and Th17 cells, J. Immunol. 2014, 192(9), 4417-4424
Non-patent Document 9: Eun-Ji Yang et al., EGCG attenuates autoimmune arthritis by inhibition of STAT3 and HIF-1α with Th17/Treg control. PLoS One. 2014, 9(2), e86062

SUMMARY OF THE INVENTION

Accordingly, the present inventors have synthesized 2-methoxy-4-(3-(4-methoxyphenyl)prop-1-en-1-yl)phenol having a novel structure, and found that the compound has an influence on a mechanism of STAT3 activation, and also performed various experiments on the use of the compound, and found that the compound has therapeutic and prophylactic effects when used to treat various inflammatory diseases including arthritis. Therefore, the present invention has been completed based on these facts.

Accordingly, it is an aspect of the present invention to provide a pharmaceutical composition for treating or preventing inflammatory diseases, which includes 2-methoxy-4-(3-(4-methoxyphenyl)prop-1-en-1-yl)phenol having a novel structure or a pharmaceutically acceptable salt thereof as an active ingredient.

It is another aspect of the present invention to provide a pharmaceutical composition for treating or preventing arthritis, which includes 2-methoxy-4-(3-(4-methoxyphenyl)prop-1-en-1-yl)phenol having a novel structure or a pharmaceutically acceptable salt thereof as an active ingredient.

To solve the above problems, according to one aspect of the present invention, there is provided a pharmaceutical composition for treating or preventing inflammatory diseases, which includes 2-methoxy-4-(3-(4-methoxyphenyl)prop-1-en-1-yl)phenol represented by the following Formula 1 or a pharmaceutically acceptable salt thereof as an active ingredient.

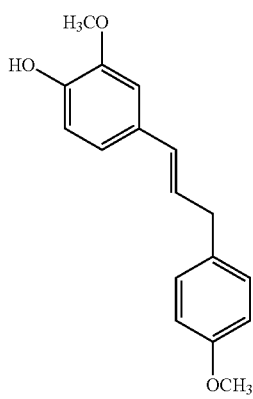 [SMILES: COc1ccc(C/C=C/c2ccc(O)c(OC)c2)cc1]

[Formula 1]

According to another aspect of the present invention, there is provided a pharmaceutical composition for treating or preventing arthritis, which includes 2-methoxy-4-(3-(4-methoxyphenyl)prop-1-en-1-yl)phenol represented by the following Formula 1 or a pharmaceutically acceptable salt thereof as an active ingredient.

In this case, the composition may be used to prevent or treat STAT3-mediated diseases.

DETAILED DESCRIPTION OF THE INVENTION

Figure 1:
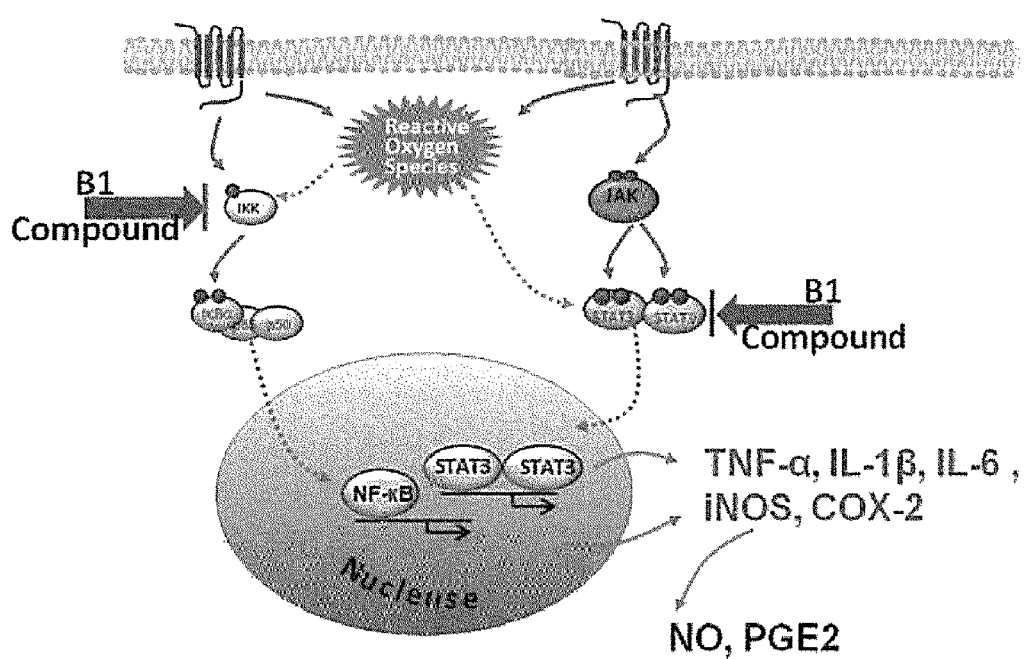
FIG. 1 is a schematic diagram showing a mechanism of NF-κB and STAT3 pathways.

According to the present invention, a new use of novel 2-methoxy-4-(3-(4-methoxyphenyl)prop-1-en-1-yl)phenol represented by the following Formula 1 is provided.

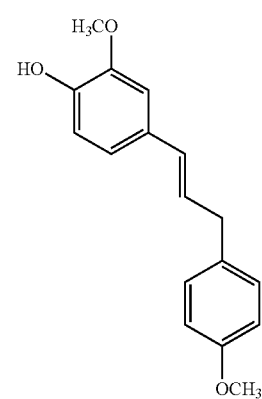

[Formula 1]

The active ingredient is named 2-methoxy-4-(3-(4-methoxyphenyl)prop-1-en-1-yl)phenol (hereinafter referred to as 'MMPP'), and has a molecular formula of $C_{17}H_{18}O_3$ and a molecular weight of 270.3 g/cm$^3$.

The MMPP includes optical isomers, stereoisomers, polymorphs, racemic mixtures, solvates, hydrates, metabolites, and pharmaceutically acceptable salts thereof. Preferably, the MMPP may be (E)-2-methoxy-4-(3-(4-methoxyphenyl)prop-1-en-1-yl)phenol.

The MMPP plays part in the activity of STAT3 (signal transducer and activator of transcription3).

STAT3 is a protein that remains inactivated in the cytoplasm, binds to a DNA base sequence as a part of a group referred to as a 'DNA binding factor,' and serves to regulate a transcription process in which genetic information in DNA is transferred to RNA strands.

Accordingly, STAT3 participates in the immune response as well as the inflammatory response to play a pivotal role in connection with arthritis or cancer.

In connection with the inflammatory response, STAT3 is a factor that plays a critical role in IL-6-induced synovial infiltration in inflammatory arthritis and is important in directly regulating the expression of oxidants or inflammatory mediators such as NO, iNOS, COX-2, IL-6, IL-1, etc.

Activation of STAT3 occurs by phosphorylating a tyrosine residue in a STAT3 transactivation domain by means of various growth factors and cytokines. Such phosphorylated STAT3 (p-STAT3) enters the nuclei to induce expression of a wide range of target genes associated with the inflammatory response and tumorigenesis.

In particular, STAT3 is an important transcription factor that interacts with NF-kB and participates in inflammation and immune response.

STAT3 forms a complex with p65 of NF-kB serving to inhibit the transcriptional activity of an iNOS gene to mediate a physical/functional interaction with NF-kB, and then stimulates cells together with the inflammatory mediators and cytokines. Once such NF-kB and STAT3 are activated, they regulate expression of anti-apoptotic, proliferation-promoting and immune response genes.

In the present invention, the compound of Formula 1 may have various ensured therapeutic and prophylactic effects against various inflammatory diseases without any side effects caused by direct inhibition of TNF-α, which has been regarded as the drawbacks of the conventional therapeutic agents, by inhibiting the activities of IKK and STAT3 prior to an inflammation expression phase to intrinsically interrupt generation of TNF-α.

Inflammatory diseases, regardless of the cause of disease development, may be treated by application of the compound of Formula 1, and thus denote the concept of encompassing diseases accompanying inflammation caused by various stimulants, which cause a series of inflammatory responses, such as NO, iNOS, COX-2, PGE2, TNF-α, IkB, etc.

Specifically, the inflammatory diseases may include one or more selected from the group consisting of septicemia, septic shock; rheumatoid arthritis, osteoarthritis, ankylosing spondylitis; vasculitis, pleurisy, pericarditis, ischemia-related inflammation, inflammatory aneurysms; nephritis; hepatitis; chronic pulmonary inflammatory diseases; bronchial inflammation, rhinitis; dermatitis; gastritis; colitis, irritable bowel syndrome; and fevers and myalgia caused by infection, but the present invention is not limited thereto.

Preferably, the compound of Formula 1 is especially effective in preventing or treating arthritis. The arthritis may include osteoarthritis, rheumatoid arthritis, and pyogenic arthritis, particularly rheumatoid arthritis, but the present invention is not limited thereto.

The severity of rheumatoid arthritis (RA) varies depending on chronic joint inflammation, and various degrees of erosion of bone and cartilage. Reactive oxygen species (ROS) generation and inflammatory responses are associated with RA. They have an influence on production of pro-inflammatory cytokines including interleukin-1 (IL-1), interleukin-6 (IL-6), and TNF-α, and thus play an important role in development of RA.

The transcription factor, NF-κB, serves to regulate expression of the pro-inflammatory cytokines and generation of oxidative and inflammatory mediators, and develop RA. In particular, a high level of NF-κB is observed in patients with RA, compared to the general population. The onset of rheumatoid arthritis is significantly reduced in p50-deficient mice, compared to wild-type mice. Similarly, joint tissues are protected from rheumatoid arthritis-induced osteolysis in the case of the p65-deficient mice. Therefore, NF-κB may be a target of a drug suitable for patients with RA.

It has been known that STAT3 mainly mediates chronic inflammation and articular destruction in rheumatoid arthritis.

Potent phosphorylation occurs in synovial tissues of the patients with RA. Overexpression of STAT3 is observed in synoviocytes and lymphocytes of the patients with RA, compared to those of the general population. However, overexpression of dominant negative STAT3 in the joint effectively improves a collagen-induced arthritis (CIA) model. Further, STAT3 is important for proliferation of synovial fibroblasts, and severely induces inflammation and articular destruction through a persistent action on the osteoclasts. Activation of STAT3 acts as a main factor for RA-related symptoms by inducing amplification of cytokines. Accordingly, it has been known that various anti-oxidative and anti-inflammatory compounds such as tofacitinib, epigallocatechin-3-gallate (EGCG), and methotrexate are effective in treating RA by inhibiting STAT3 signaling. For example, CP690,550 treatment inhibits a cytokine loop by STAT3 suppression, and thus increases the onset of RA. Therefore, STAT3 is a potential therapeutic target, and prevents chronic inflammation and articular destruction in RA. Also, it has been known that STAT3 complementarily interacts with NF-κB. For example, the functional mutual relationship between NF-κB and STAT3 in immune cells regulates production of pro-inflammatory cytokines. In addition, it has been known that the mutual relationship between NF-κB and STAT3 is mediated in the onset of RA by production of IL-6.

The compound of the present invention has anti-oxidative features, and thus has an anti-inflammatory response by inhibiting phosphorylation of STAT3 to inhibit the activity of STAT3. Also, the compound has an effect of reducing bone destruction and fibrosis in rheumatoid articular tissues.

According to experimental examples of the present invention, it is confirmed that MMPP may alleviate rheumatoid arthritis by inhibiting a STAT3 pathway when MMPP is administered to mice in a mouse model in which rheumatoid arthritis is induced.

According to the present invention, when the compound represented by Formula 1 is applied to a pharmaceutical composition, the composition may include the compound or a pharmaceutically acceptable salt thereof as an active ingredient.

The pharmaceutically acceptable salt includes salts of organic acids, for example, formic acid, acetic acid, propionic acid, lactic acid, butyric acid, isobutyric acid, trifluoroacetic acid, malic acid, maleic acid, malonic acid, fumaric acid, succinic acid, monoamide succinate, glutamic acid, tartaric acid, oxalic acid, citric acid, glycolic acid, glucuronic acid, ascorbic acid, benzoic acid, phthalic acid, salicylic acid, anthranilic acid, benzene sulfonic acid, p-toluenesulfonic acid, and methanesulfonic acid; and salts of inorganic acids, for example, hydrochloric acid, bromic acid, sulfuric acid, phosphoric acid, nitric acid, carbonic acid, and boric acid.

The aforementioned acid addition salts may be prepared using a conventional method, for example, prepared by dissolving the compound of Formula 1 in an excessive amount of an aqueous acid solution, precipitating a salt of the compound with a water-miscible organic solvent, for example, methanol, ethanol, acetone, or acetonitrile. Also, the acid addition salts may be prepared by evaporating the solvent and an excessive amount of an acid from the mixture, and then drying the mixture or filtering the precipitated salt by suction.

Also, a pharmaceutically acceptable metal salt may be prepared using a base. An alkali metal salt or an alkaline earth metal salt is, for example, obtained by dissolving the compound in an excessive amount of an alkali metal hydroxide or alkaline earth metal hydroxide solution, filtering an insoluble compound salt, and evaporating and drying the filtrate. In this case, it is desirable that a lithium, sodium, potassium or calcium salt is prepared as the metal salt in a pharmaceutical aspect. Also, a silver salt corresponding to the metal salt is obtained by allowing an alkali metal salt or an alkaline earth metal salt to react with a suitable silver salt (for example, silver nitrate).

Further, a pharmaceutically acceptable salt may be prepared using an amino acid. For example, it is desirable that a natural amino acid such as glycine, alanine, phenylalanine, valine, lysine, glutamic acid, etc. is prepared as the amino acid salt in a pharmaceutical aspect.

For administration, the composition of the present invention may include a pharmaceutically acceptable carrier, an excipient, or a diluent in addition to the aforementioned active ingredient.

The carrier, excipient and diluent that may be used in the present invention may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium, a stearate, and mineral oil.

The composition of the present invention may be formulated into oral preparations such as a powder, a granule, a tablet, a capsule, a suspension, an emulsion, syrup, an aerosol, etc., and forms of a liquid for external use, a suppository, and a sterile injectable solution using conventional methods.

Specifically, when formulated, the composition may be prepared using a diluent or excipient typically used in the art, such as a filler, a bulking agent, a binder, a wetting agent, a disintegrating agent, a surfactant, etc. A solid preparation for oral administration includes a tablet, a pill, a powder, a granule, a capsule, etc., but the present invention is not limited thereto. Such a solid preparation may be prepared by mixing at least one excipient, for example, starch, calcium carbonate, sucrose or lactose, gelatin and the like, with the compound.

Also, lubricants such as magnesium stearate, talc and the like may be used in addition to the simple excipients. In this case, the liquid preparation includes various excipients, for example, a wetting agent, a sweetening agent, a flavoring agent, a preservative, and the like in addition to the liquids for oral administration, liquid paraffin, etc.

A preparation for parenteral administration includes a sterile aqueous solution, a non-aqueous solvent, a suspension, an emulsion, a freeze-dried preparation, and a suppository. Propylene glycol, polyethylene glycol, and a vegetable oil such as olive oil, an injectable ester such as ethyl oleate, and the like may be used as the non-aqueous solvent and the suspending agent. Witepsol, Macrogol, Tween 61, cacao butter, laurin butter, glycerogelatin, and the like may be used as a base of the suppository.

The composition of the present invention is administered in a pharmaceutically effective amount. In the present invention, the term "pharmaceutically effective amount" refers to an amount sufficient to treat a disease at a reasonable benefit/risk ratio applicable to any medical treatment and sufficient to cause no side effects. In this case, a level of the effective dose may be determined depending on the health condition of a patient, the type and severity of a disease, the activity of a drug, the sensitivity to the drug, an administration mode, an administration time, a route of administration, and a secretion rate, a therapeutic period, factors including drugs to be blended or used together, and other factors well known in the field of medicine. The composition of the present invention may be administered as an individual therapeutic agent, or may be administered in combination with other therapeutic agents. In this case, the composition may be administered sequentially or concurrently with conventional therapeutic agents, and may be administered in a single dose or multiple doses. By considering all the aforementioned factors, it is important to administer the composition at a dose in which the maximum effect can be achieved at the minimum amount without any side effects. Thus, the dose of the composition may be easily determined by those skilled in the related art.

Specifically, the effective dose of the compound in the composition of the present invention may vary depending on the age, sex, and weight of a patient. In general, the composition may be administered at a dose of 1 to 100 mg/kg, preferably 3 to 30 mg/kg daily or every other day or once or three times a day. However, because the dose of the composition may be increased or decreased, depending on a route of administration, the severity of a disease, the sex, weight, and age of a patient, etc., the dosage is not intended to limit the scope of the present invention in any way.

The composition of the present invention may be administered to a mammal such as a mouse, a rat, cattle, a human, etc. via various routes of administration. It is possible to expect all administration modes. For example, the composition may be orally, intrarectally or intravenously administered, or may be administered by intramuscular, subcutaneous, intrauterine or intracerebroventricular injection.

Hereinafter, the configurations of the present invention will be described in further detail with reference to embodiments thereof. However, it should be understood that the following embodiments disclosed herein are provided to aid understanding the present invention, and are not intended to limit the scope of the present invention.

EXAMPLES

Preparative Example 1. Preparation of 2-methoxy-4-(3-(4-methoxyphenyl)prop-1-en-1-yl)phenol 4-Iodo-2-methoxyphenol (500 mg, 2.0 mmol) and 4-allylanisole (313 mg, 2.0 mmol) were put into a 25 mL flask reactor, and triphenyl phosphine (105 mg, 0.4 mmol), Pd(OAc)$_2$ (44.9 mg, 0.2 mmol), and tributylamine (451 mg, 1.9 mmol) were then added thereto. Thereafter, the resulting mixture was reacted at 45° C. for 2 hours.

The resulting compound was purified through flash silica gel chromatography (hexane/ethyl acetate, 3:1, v/v) to prepare the title compound (119 mg, Yield: 22%, dark brown liquid).

High resolution mass spectrometry (HRMS; ESI) m/z $[M+H]^+$ cacld. 271.1329, found 271.1332

$^1$H-NMR: d (CDCl$_3$) 7.32 (d, 2H, J=8.0 Hz), 6.88 (d, 1H, J=9.0 Hz), 6.86 (d, 2H, J=9.0 Hz), 6.76 (d, 1H, J=8.0 Hz), 6.75 (s, 1H), 6.40 (d, 1H, J=16.0 Hz), 6.21 (dt, 1H, J=16.0 Hz, J=6.5 Hz), 5.54 (s, 1H), 3.89 (s, 3H), 3.82 (s, 3H), 3.48 (d, 2H, 7.0 Hz)

Evaluation Methods

Methods used in the experimental examples are summarized, as follows.

1. Pull-Down Assay

As a method for isolating a protein complex, a pull-down assay is an assay for checking a protein-protein interaction. To identify a protein interacting with MMPP, MMPP was bound to cyanogen bromide epoxy-activated Sepharose 6B (Sigma, St Louis, Mo., United States).

2. Construction of plasmid: A coding region of *Mus musculus* STAT3 was amplified by PCR using full-length *Mus musculus* STAT3 cDNA as a template. The purified PCR product was doubly digested with EcoRI and XhoI, and then subcloned into a pcDNA3.1 vector. The pcDNA3.1 plasmid includes a cytomegalovirus promoter, a pUC origin of replication, and an ampicillin-resistant gene. STAT3 (T456A) mutagenesis was performed at Cosmo Genetech Co., Ltd. (Seoul, Korea), and the mutations were systematically checked by sequencing. RAW264.7 cells were seeded in a 24-well plate at a density of $1 \times 10^5$ cells/well. The cells were grown for 24 hours to reach 90% confluence, and the cells were infected with the mutant STAT3 (T456A) plasmid (Cosmo Genetech Co., Ltd., Seoul, Korea) using a mixture of the plasmid and lipofectamine in PTI-MEN. The infected cells were treated with LPS (1 µg/mL), and different concentrations of MMPP (1 to 4 µg/mL) for 12 hours. The prepared samples were subjected to Western blotting.

3. RAW 264.7 cell culture: As a mouse macrophage-like cell line, RAW 264.7 cells were purchased from the American Type Culture Collection (Cryosite, Lane Cove, NSW, Australia). A Dulbecco's modified Eagle's medium (DMEM), penicillin, streptomycin, and fetal bovine serum were purchased from Gibco Life Technologies (Rockville, Md., USA). RAW 264.7 cells were cultured at 37° C. under a condition of 5% $CO_2$ in a DMEM medium supplemented with 10% fetal bovine serum, 100 U/mL penicillin, and 100 m/mL streptomycin.

4. Human synoviocyte culture: The research protocol and human tissue cells used in the study were approved by the College of Medicine of Soon Chun Hyang University Medical Center. Cells were obtained from patients with rheumatoid arthritis diagnosed according to the American College of Rheumatology classification criteria revised in 1987. Synovial tissue samples are obtained from knee joints of patients with long-term rheumatoid arthritis (two males and two females, an average age of 65±21.3 years, and an average onset period of 10 years or more). FLS (Fibroblast-like synoviocytes) were cultured as described above. Simply, the FLSs were cultured in a culture dish (Nalge Nunc International, Rochester, N.Y., USA) containing a DMEM culture medium (Gibco Life Technologies) supplemented with heat-activated FBS (Gibco Life Technologies) and 50 $U·mL^{-1}$ penicillin/streptomycin. For all cultures and an incubator, the culture was performed at 37° C. in an incubator under a 5% $CO_2$ atmosphere. The medium was replaced every three days. The cells between $5^{th}$ and $10^{th}$ passage were used.

5. Cell activity assay: To measure the number of cells, the cells were put into a 24-well plate ($5 \times 10^4$ cells/well). The cells were treated with trypsin, and centrifuged at 1,500 rpm for 5 minutes to obtain pellets. Thereafter, the pellets were re-suspended in 10 mL of PBS. Subsequently, 0.1 mL of 0.2% trypan blue was added to the cell suspension (0.9 mL). Then, one drop of the suspension was added to a Neubauer chamber, and viable cancer cells were counted. The stained cells were considered to be dead, and the cells which were not stained with Trypan blue were considered to be viable, and then counted. Each assay was performed in triplicate.

6. Nitrite assay: RAW 264.7 cells were added to a 96-well plate at a density of $1 \times 10^4$ cells/well, and LPS (1 mg/mL) and TNF-α (10 ng/mL) were added or not added for 24 hours in the presence or absence of various concentrations of MMPP. Accumulation of nitrites in a supernatant was analyzed using a nitric oxide assay kit commercially available from iNtRON Biotechnology (Seongnam, Korea).

7. PEG2 and cytokine Assays: A PGE2 assay was carried out in the cultured RAW 264.7 cells using an ELISA kit (commercially available from R&D Systems).

8. ROS Assay: An ROS assay was carried out using an ELISA kit (commercially available from Cell Biolabs Inc.).

9. Cell infection: RAW 264.7 cells ($5 \times 10^4$ cells/well) were added to a 24-well plate, and transiently infected with a STAT3-luciferase reporter plasmid and an iNOS-luciferase reporter plasmid using a Lipofectamine PLUS and plasmid mixture in OPTI-MEN.

10. EMSA assay (Electromobility shift assay): RAW 264.7 cells were cultured for 24 hours to perform an EMSA assay. The relative density of a protein band was scanned using MyImage, and qualitatively analyzed using Labworks 4.0 software (UVP, Inc.).

11. Luciferase activity assay: RAW264.7 cells added to a 24-well plate at a density of $1 \times 10^5$ cells/well. After 90% confluence, the cells were transiently infected with STAT3 siRNA (Santa Cruz Biotechnology) or a mutant STAT3 (T456A) plasmid using a mixture of STAT3 siRNA (Santa Cruz Biotechnology) or a mutant STAT3 (T456A) plasmid and WelFect-EX PLUS in OPTI-MEN. The infected cells were treated with LPS (1 µg/mL) and different concentrations of MMPP (1 to 4 µg/mL) for 12 hours. The luciferase activity was measured using a luciferase assay kit (Promega, Madison, Wis., USA).

12. Western blotting assay: A whole cell lysate, a cytosolic extract, and a nuclear extract were obtained. SDS-PAGE and Western blotting assays were carried out as disclosed in published Documents 1 and 2. Simply speaking, the cells were seeded in a 6-well plate at a density of $5 \times 10^5$ cells/well, and cultured for 24 hours. Thereafter, the cells were treated with MMPP or DMSO for 24 hours. After the treatment, the cells were washed twice with PBS, and then lyzed. Proteins of the lyzed cells were separated on 10 to 15% SDS-PAGE. The proteins were transferred to a PVDF membrane, and the PVDF membrane was blocked at room temperature for 2.5 hours in a TB S/T buffer containing 5% skim milk. The membrane to which the proteins were transferred was analyzed using, as primary antibodies, murine monoclonal antibodies against Cdk2, Cdk4, Cdk6, cyclin B1, cyclin D1, cyclin E1, Bcl-2, Bax, caspase-3, caspase-8, STAT3, phspho-STAT3, (3-actin, and histone h1. Expression of the proteins was visualized using a chemiluminescence reagent (Amersham Pharmacia Biotech, Inc., Buckinghamshire, UK), and measured using a digital chemiluminescence imaging system equipped with a CCD camera (Fusion-FX, Fisher BioTech, Ltd., Wembley, Australia).

13. Splenocyte NO assay: A spleen was collected, and cut into small sections. Thereafter, the spleen sections were passed through a tissue sieve (200 mesh/2.5 cm) to prepare a single-cell suspension in PBS. The suspension was centrifuged at 1,500 rpm for 4 minutes, and a supernatant was then removed. The precipitate was washed three times with PBS, and then suspended in 2 mL of an RPMI1640 complete media. The cells was stained and measured by trypan blue dye exclusion. The cells were counted to have a cell density of $3 \times 10^6$ cells/mL. The $3 \times 10^6$ cells were suspended in RPMI 1640 containing 5 μg/mL of ConA, and cultured at 37° C. under a 5% $CO_2$ atmosphere. After 48 hours, the cells were suspended for 30 minutes in RPMI 1640 containing 10 mg/mL of methyl-α-D-pyranoside. The cells were collected, and washed three times with PBS. The cells were suspended at a density of $1 \times 10^6$ cells/well in 1 mL of RPMI 1640 containing 10 pg/mL of the IL-2 cytokine, and cultured at 37° C. for 24 hours under a 5% $CO_2$ atmosphere. An NO assay was as described above.

14. Induction of rheumatoid arthritis in C57BL/6 mice: To induce rheumatoid arthritis, anti-collagen-II mAbs (CII-Ab, Arthrogen-CIA Arthritogenic Monoclonal Antibody, #53010: Chondrex, Inc., WA, USA) were intraperitoneally (i.p.) injected into 7-week-old male mice on the first day, and 50 μg of LPS was injected on the third day. To evaluate the severity of arthritis, a scoring system was applied according to the criteria.

0. No erythema and swelling are observed.
1. Slight erythema is observed in tarsals and ankle joints.
2. Slight erythema and swelling are observed from an ankle joint to the midfoot.
3. Erythema and swelling extending from ankle joints to the metatarsals are observed.
4. Erythema and severe swelling were observed throughout the ankles, feet, and fingers.

The sum of final scores was recorded daily until the sum reached 16. On the 18th day, each of the mice was anesthetized, and then located on a radiographic view box. Thereafter, a location of each of the mice was adjusted so that the mouse was disposed at a distance of 90 cm from an X-ray source. The radioanalysis on hind legs with arthritis was performed by irradiating the hind legs at 40 KW for 0.01 seconds using an X-ray machine (BLD-150RK, Hradec Kralove, Czech Republic).

15. Immunohistochemical assay: An immunohistochemical assay was carried out using an avidin-biotin-peroxidase method known in the art. Each of joint tissue samples collected from the mice was fixed with formalin, and embedded in paraffin. These samples were continuously microtomed into sections with a thickness of 4 μm. Each of the sections was stained with haematoxylin/eosin (H&E), anti-COX-2 and anti-iNOS antibodies (Caymen Chemical, Ann Arbor, Mich.).

16. Blood count test: The total number of neutrophiles and monocytes was counted from heparinized blood using a HIE cell counter (Technicon Instruments, Miles Laboratories, Tarrytown, N.Y.).

17. Molecular modeling: MMPP docking research was performed using AutoDock. An unphosphorylated STAT3 monomer was extracted from an X-ray crystal structure of a STAT3 dimer core fragment (PDB ID: 3CWG), and used. First, a polar hydrogen atom was added to a STAT3 monomer using AutodockTools. A 3D structure of MMPP was designed using ChemBio3D and Discovery Studio 3.5 Client, and an MMPP ligand was allowed to rotate freely from 8 rotatable single bonds during a molecular simulation. STAT3 in a grid box was located at the center, and the size of the grid box was adjusted so that the grid box included all of the monomer. A docking experiment was carried out several times at various default values of 16, 24, 32, 40, and 60, depending on a binding mode. An image of MMPP and STAT3 bound therebetween was obtained using Discovery Studio Visualizer 4.0.

18. Data analysis: An ANOVA statistical analysis was carried out with SPSS version 18.0. Data using a Shapiro-Wilk normality test, and a post-hoc Tukey test was then carried out for comparison between MMPP and STAT3. The results obtained for statistical significance are represented as average±standard deviation (SD) ($P<0.05$).

Experimental Example 1. Cell Toxicity Assay (MTT Assay)

As mouse macrophages, RAW 264.7 macrophages were cultured in a DMEM medium supplemented with 10% FBS. 200 mL of the medium was treated with MMPP, and then stabilized for an hour.

An MTT reagent was added at a concentration of 0.5 mg/mL, and the cells were cultured at 37° C. in an incubator. After the medium was completely removed when 70% of the cells formed crystals, 100 mL of DMSO was added to dissolve the crystals. Subsequently, the optical density was measured at 550 nm.

Experimental Example 2. Analysis of Interaction Between MMPP and STAT3

Figure 2:
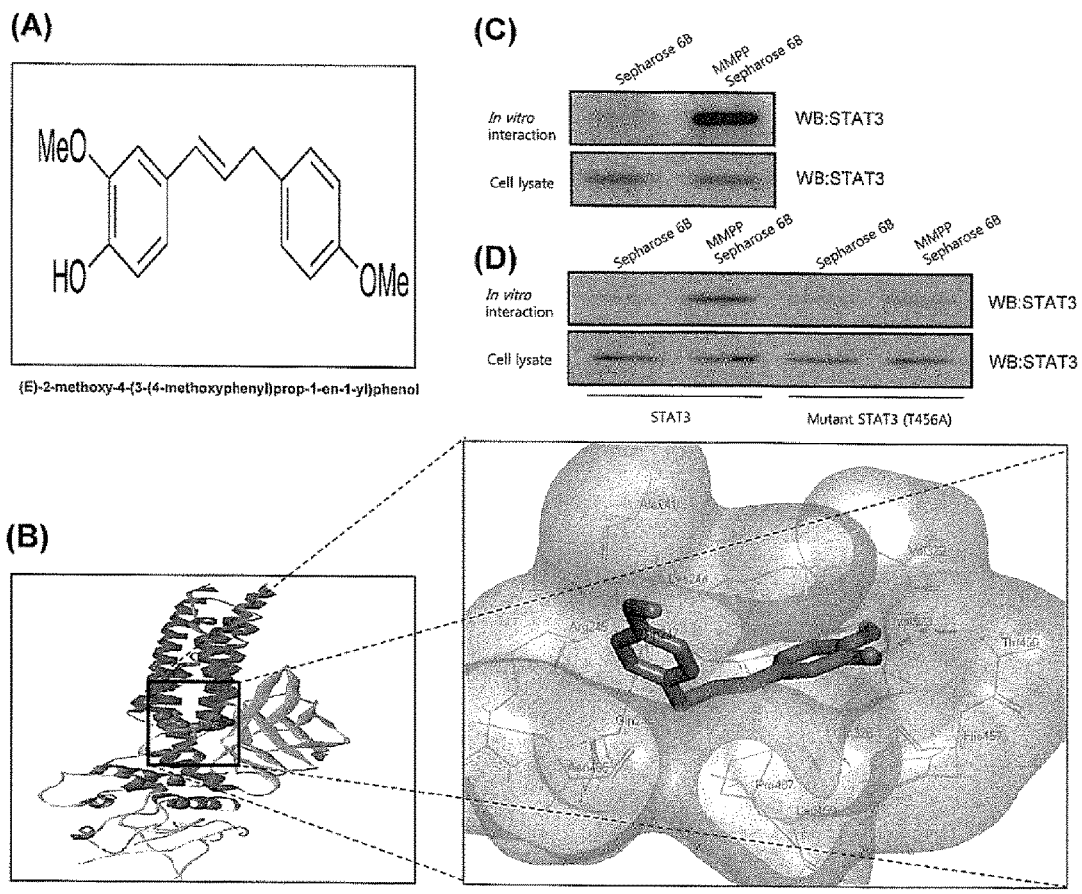
FIG. 2 shows results of a computational docking experiment between MMPP and STAT3: (A) is a chemical formula of MMPP, (B) is an image of three-dimensional (3D) modeling of binding between DNA binding domains of MMPP and STAT3, (C) shows results of pull-down assay experiments on MMPP and STAT3, and (D) shows results of pull-down assay experiments on bound STAT3 and mutant STAT3 (T456A).

In Experimental Example 2, a computational docking experiment between MMPP and STAT3 was performed according to the Induced Fit Docking of Schrodinger Suite 2011. Referring to FIG. 2(B), it can be seen that MMPP is bound to a DNA binding domain (Thr456) of STAT3 at an affinity of −8.2 kcal/mol. As a result, it can be seen that MMPP inhibited the kinase activity of STAT3 by blocking DNA binding of STAT3. An image of FIG. 2 was formed by the UCSF Chimera program (Schrodinger, 2011).

To check the interaction between MMPP and STAT3, a pull-down assay was carried out. MMPP was conjugated to epoxy-activated Sepharose 6B. A pull-down assay was performed using an interaction between a cell lysate containing a recombinant STAT3 protein or a STAT3 protein and MMPP conjugated to Sepharose 6B beads. Referring to FIG. 2(C), it can be seen that MMPP mediated the interaction between the cell lysate and the recombinant STAT3 protein containing STAT3 from RAW 264.7 cells. Referring to FIG. 2(D), it can also be seen that the binding of MMPP to mutant STAT3 Thr456A was reduced, compared to the STAT3.

Experimental Example 3. Anti-Inflammatory Effect (In Vitro) of MMPP on Reaction Mechanism of STAT3

In Experimental Example 3, a mutant type of mutant STAT3 (T456A) was used to determine the involvement in the inflammatory response of MMPP in RAW 264.7 cells.

RAW 264.7 cells were transformed with mutant STAT3 (T456A) plasmid DNA. After 24 hours, the transformed cells were treated with 1 mg/mL of lipopolysaccharides (LPS) alone or a combination of LPS and MMPP.

Figure 3:
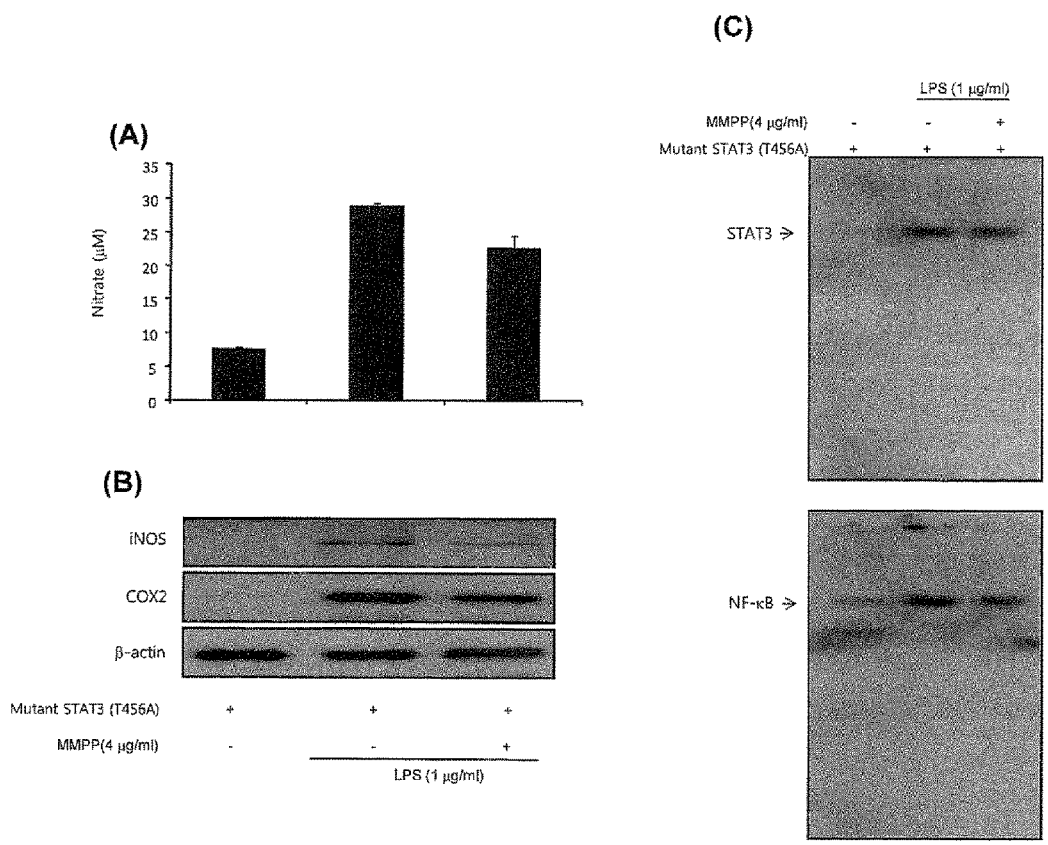
FIG. 3 shows results of Experimental Example 3 as an experiment on an anti-inflammatory effect of MMPP by participation in a STAT3 pathway; (A) shows experimental results of NO generation according to a concentration of LPS, (B) shows result of experiments on iNOS and COX2, and (C) shows experimental results showing DNA binding activities of STAT3 and NF-κB.

When the RAW 264.7 cells were transformed with the mutant STAT3 (T456A), NO generation, iNOS and COX2 expression, and STAT3 and NF-κB activities were measured. Referring to FIG. 3(C), it can be seen that the STAT3 and NF-κB activities disappeared in the RAW 264.7 cells by mutation of STAT3 (T456A).

Referring again to FIGS. 3(A) and (B), the NO generation and the iNOS and COX2 expression disappeared in the RAW 264.7 cells by the mutation of STAT3 (T456A). These results show that MMPP was covalently bound to Thr 456 in a DNA binding site of STAT3, and thus the STAT3 activity was inhibited by preventing the DNA binding activity of STAT3.

Experimental Example 4. Analysis of Inhibitory Effect of MMPP on LPS-Induced Anti-Inflammatory Response in RAW 264.7 Cells In Experimental Example 4, a luciferase activity assay was carried out to determine whether MMPP inhibited generation of LPS-induced infective factors in RAW 264.7 cells. RAW 264.7 cells were transiently infected with an iNOS-luciferase construct, treated with LPS (1 µg/mL) alone or a combination of MMPP and LPS, and then activated for 12 hours.

The same amount of the total proteins (20 µg/Lane) from the cells cultured for 12 hours was subjected to 10% SDS-PAGE, and expression of iNOS and COX-2 was detected by Western blotting using antibodies. A (3-actin protein was used as the control.

Morphological changes of the cells were observed under a microscope, and the cell viability was determined using an MTT assay.

Figure 4:
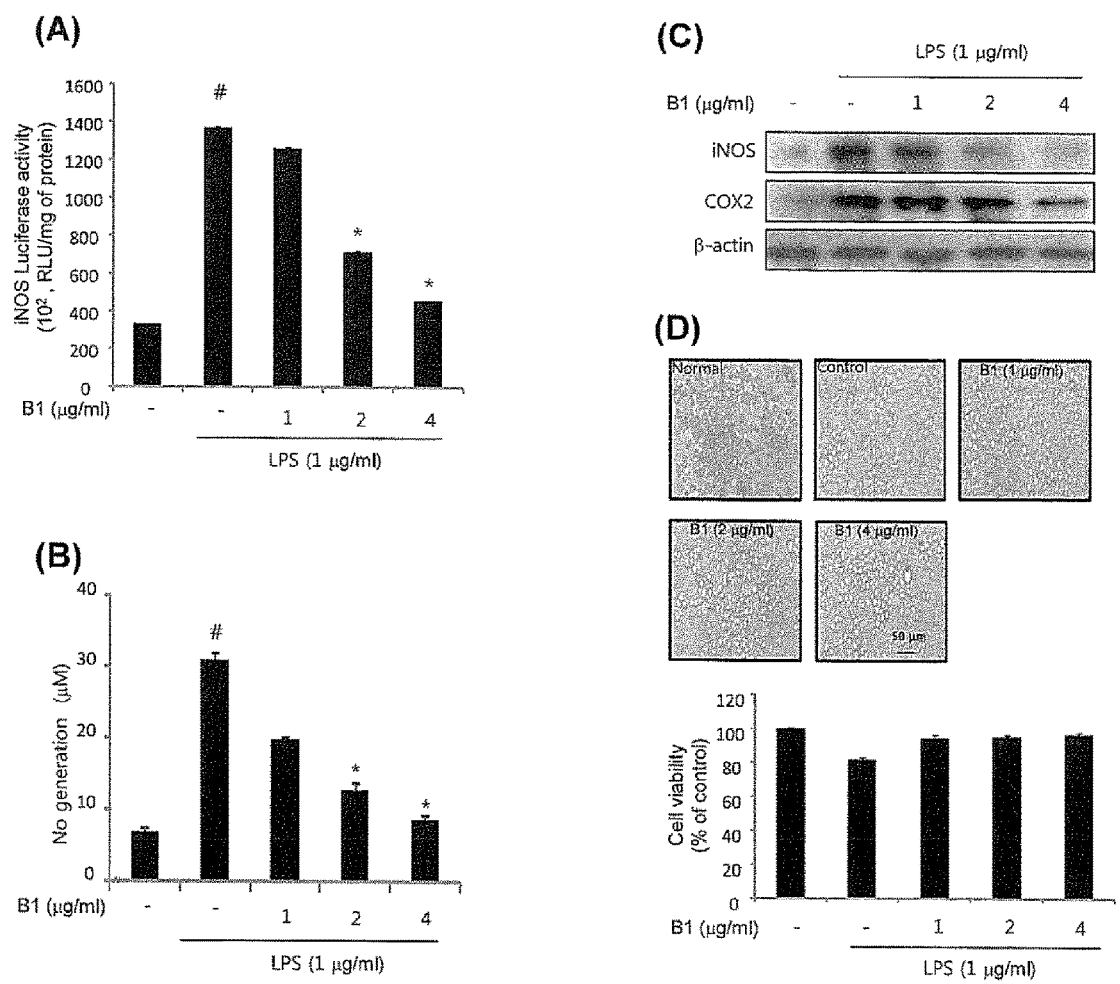
FIG. 4 shows results of Experimental Example 4 as an experiment on an inhibitory effect of MMPP on LPS-induced NO generation, expression of iNOS and COX-2, and cell viability: (A) shows experimental results showing iNOS activity according to a concentration of MMPP, (B) shows experimental results for NO generation according to concentration of MMPP, (C) shows experimental results for iNOS and COX2 expression, and (D) is an image and graph showing cell viability according to concentration of MMPP.
Figure 5:
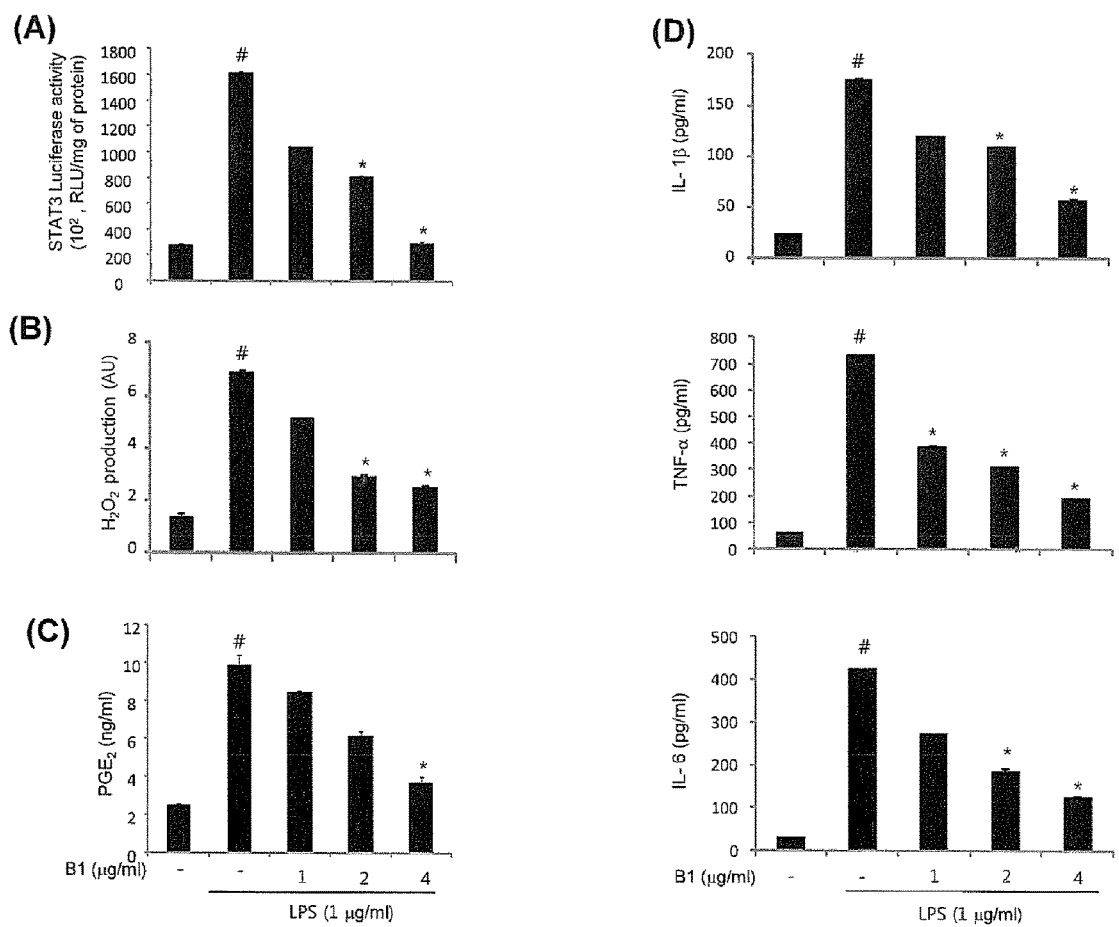
FIG. 5 shows results of Experimental Example 4: According to the concentration of MMPP, (A) is a graph plotted for STAT3 luciferase activity, (B) is a graph plotted for hydrogen peroxide generation-related results, (C) is a graph plotted for PGE2-related results, (D) shows a graph plotted for IL-1β, (E) is a graph plotted for TNF-α results, and (F) shows a graph plotted for IL-6-related results.

It can be seen that, when the cells were treated with a combination of LPS (1 mg/mL) and MMPP (0 to 4 mg/mL), the iNOS luciferase activity (FIG. 4(A)), the NO generation (FIG. 4(B)), and the iNOS and COX-2 expression (FIG. 4(C)) in the LPS-induced cells were reduced in a concentration-dependent manner. However, referring to FIG. 4(D), it can be seen that the viability of the LPS-induced RAW 264.7 cells was not affected up to 4 mg/mL. From these result, it can be seen that MMPP used herein had no toxicity.

Further, it was determined whether MMPP inhibited generation of ROS, $PGE_2$, and pro-inflammatory cytokines by inhibiting expression of related genes.

RAW 264.7 cells were transiently infected with a STAT3-luciferase construct, treated with LPS (1 µg/mL) alone or a combination of MMPP and LPS, and then activated for 12 hours. Thereafter, the luciferase activity, the ROS and PGE2 expression, and a level of pro-inflammatory cytokines were determined.

Referring to FIGS. 5(A) to (D), it can be seen that MMPP inhibited the LPS-induced STAT3 luciferase activity, the ROS and $PGE_2$ expression, and the level of pro-inflammatory cytokines (TNF-α, IL-6 and IL-1) in a concentration-dependent manner (0 to 4 mg/mL).

Experimental Example 5. Analysis of Inhibitory Effect of MMPP on NF-κB and STAT3 Activities In Experimental Example 5, it was determined whether MMPP inhibited NF-κB activity to inhibit expression of iNOS and COX-2 in RAW 264.7 cells.

RAW 264.7 cells were treated with LPS alone or a combination of LPS and MMPP for 30 minutes, and the DNA binding activities of NF-κB and STAT3 were examined using an electrophoretic mobility shift assay (EMSA). Also, the same amount of the total proteins (20 µg/Lane) was subjected to 10% SDS-PAGE, and STAT3, P-STAT3, p50, p65, IKK, IκB, and p-IκB were detected through Western blotting. A (3-actin protein or histone H was used as the control.

Figure 6:
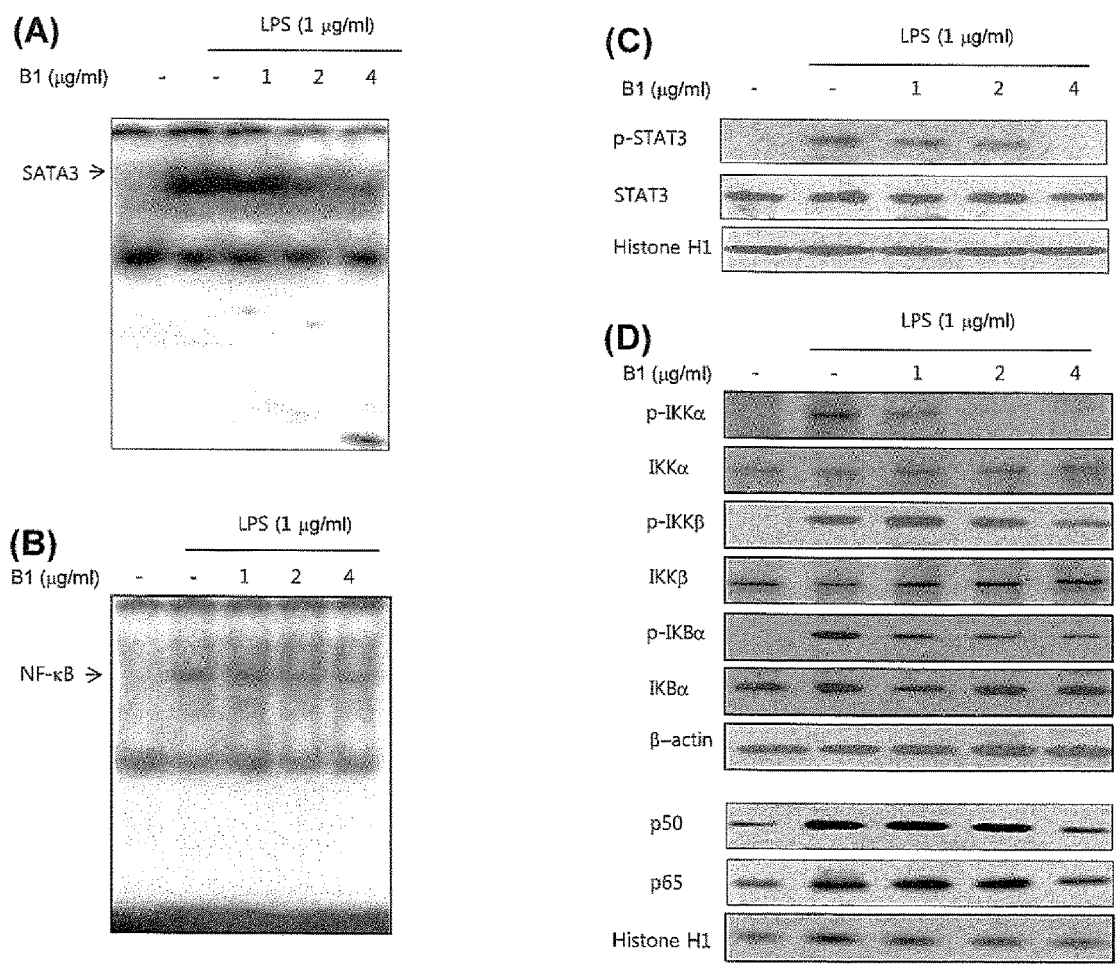
FIG. 6 shows results of Experimental Example 5: (A) shows experimental results for DNA binding activity of STAT3 according to concentration of MMPP, (B) shows experimental results for DNA binding activity of NF-κB according to concentration of MMPP, (C) is an image of the DNA binding activity of STAT3, and (D) shows experimental results for STAT3, p-STAT3, p50, p65, IKK, p-IKK, IkB, and p-IkB according to concentration of MMPP.

Referring to FIGS. 6(B) and (D), it can be seen that LPS induced potent DNA binding activity and transcriptional activity of NF-κB, nuclear translocation of NF-κB subunits p65 and p50, and IκB degradation, all of which were reduced in a concentration-dependent manner when the cells were co-treated with MMPP. In addition, referring to FIG. 6(D), it can be seen that MMPP inhibited LPS-induced phosphorylation of IKKb and IKKa. It can be seen that STAT3 is an important redox transcription factor included in the inflammatory and immune responses, and interacts with NF-κB. In this case, it was determined whether MMPP reduced STAT3 activity in the RAW 264.7 cells. The results are shown in FIGS. 6(A) and (C). Referring to FIG. 6(C), it can be seen that MMPP inhibited the LPS-induced phosphorylation of STAT3.

Experimental Example 6. Analysis of STAT3 Pathway on Pro-Inflammatory Effect of MMPP in RAW 264.7 Cells In Experimental Example 6, an effect of STAT3 siRNA on a protective effect of MMPP on LPS-induced pro-inflammatory response in RAW 264.7 cells was examined.

First, a protective effect of MMPP on the LPS-induced pro-inflammatory response was tested using RAW 264.7 cells infected with STAT3 siRNA.

The RAW 264.7 cells were infected with STAT3 siRNA. After 24 hours, the infected cells were then treated with 1 mg/mL of LPS alone or in combination with MMPP. Thereafter, the NO generation, the iNOS and COX2 expression, and the DNA binding activity of NF-κB were measured.

Figure 7:
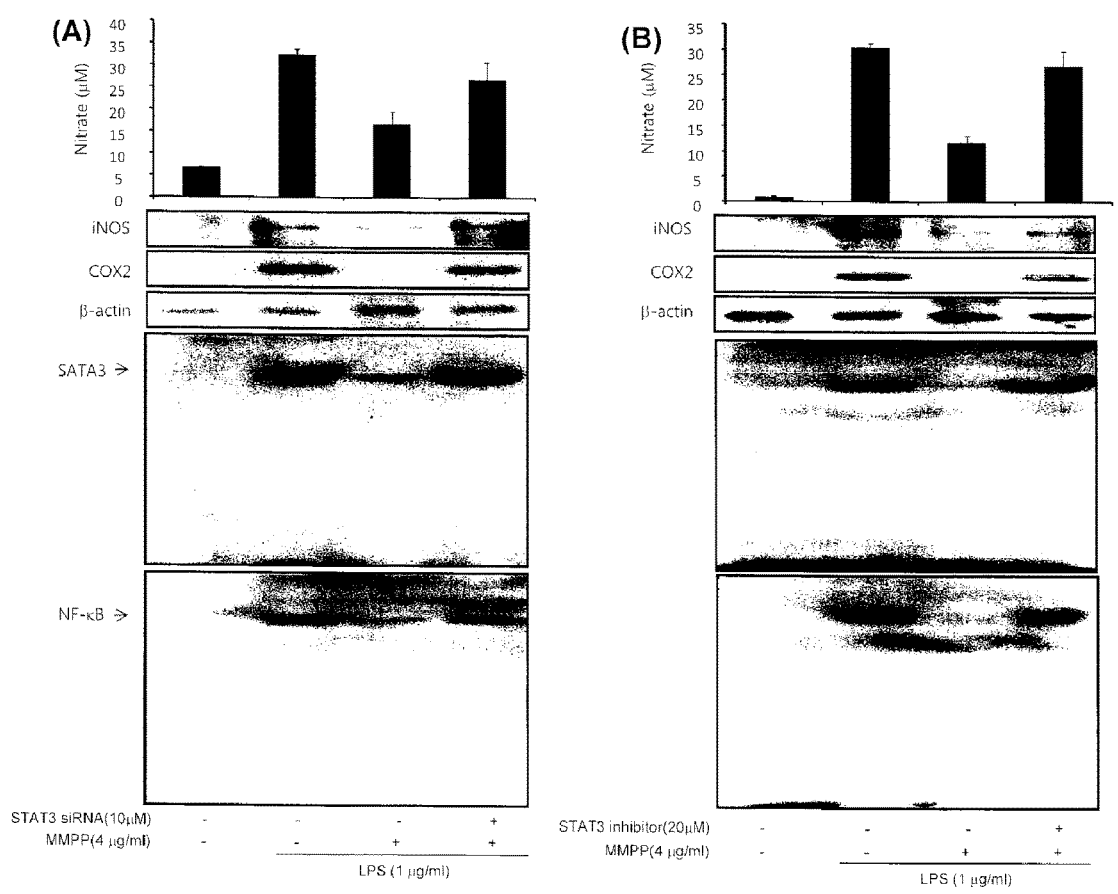
FIG. 7 shows results of Experimental Example 6: (A) is a graph and image for STAT3 and NF-κB activities in the presence/absence of MMPP, and (B) is a graph and experimental results for iNOS and COX2 in the presence/absence of MMPP.

As a result, it was revealed that STAT3 knock-down cells limited an inhibitory effect of MMPP on the LPS-induced NO generation, the iNOS and COX2 expression, and the NF-κB activity (FIG. 7(A).

Next, it was examined whether an effect of a STAT3 inhibitor in RAW 264.7 cells was limited. RAW 264.7 cells were treated with a STAT3 inhibitor (20 mM) alone or in combination with MMPP, and the NO generation, the iNOS and COX2 expression, and the DNA binding activity of NF-κB were also measured. As a result, it was revealed that the STAT3 inhibitor completely limited an inhibitory effect of MMPP on the LPS-induced NO generation, the iNOS and COX2 expression, and the NF-κB activity (FIG. 7(B)). These experimental results showed that a STAT3 pathway is very important for an anti-inflammatory effect of MMPP.

Experimental Example 7. Analysis of Inhibitory Effect on NO and ROS Generation, iNOS and COX2 Expression, and NF-κB and STAT3 Activities in TNF-α-Induced RAW 264.7 Cells In Experimental Example 7, an experiment regarding an anti-inflammatory effect of MMPP in TNF-α-treated RAW 264.7 cells was performed.

Figure 8:
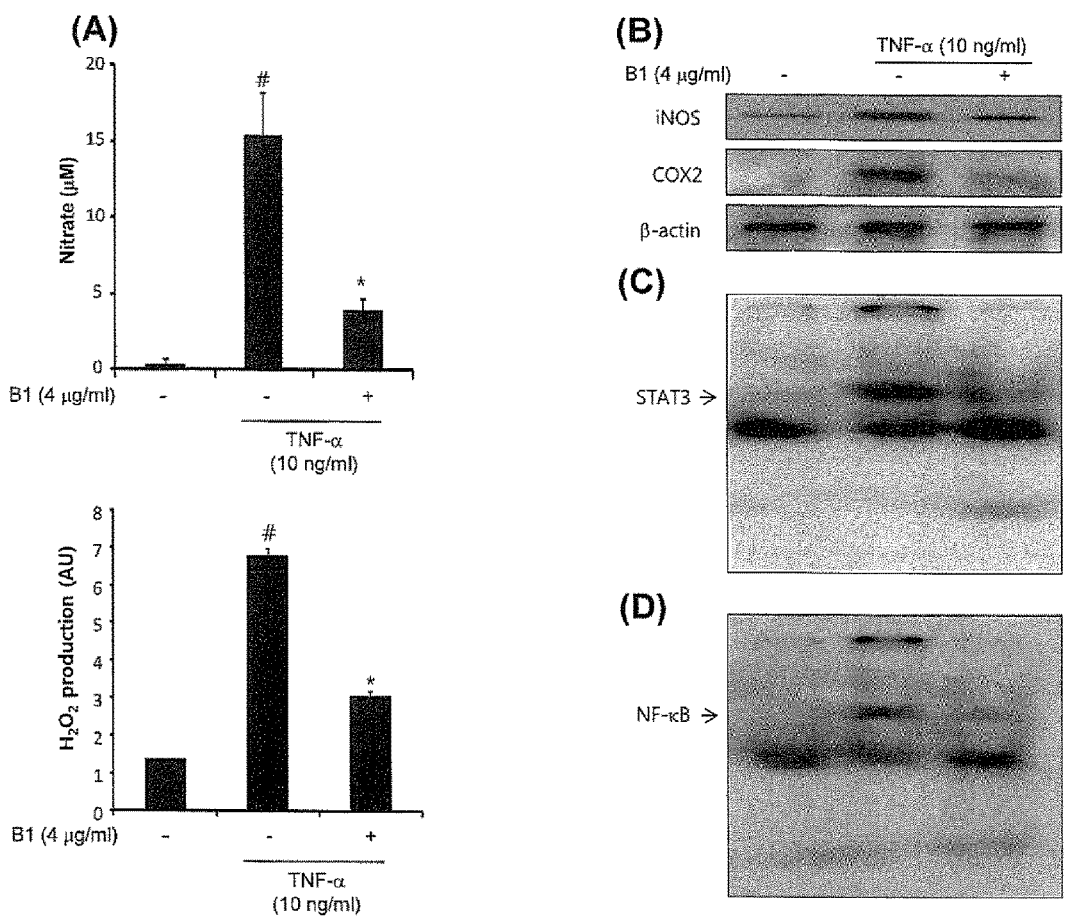
FIG. 8 shows results of Experimental Example 7: In the presence of TNF-α, (A) is a graph plotted for results of NO and hydrogen peroxide generation in the presence/absence of MMPP, (B) is a graph and image for iNOS and COX2, (C) shows experimental results for STAT3 activity, and (D) shows experimental results for NF-κB activity.

It was confirmed that, when RAW 264.7 cells were treated with TNF-α (10 ng/mL) in combination with MMPP (4 mg/mL) for 24 hours, the NO and ROS generation (FIG. 8(A)), the iNOS and COX2 expression (FIG. 8(B)), and the STAT3 and NF-κB activities (FIGS. 8(C) and (D)) induced by treatment with TNF-α (10 ng/mL) were reduced in the RAW 264.7 cells. These results showed that the anti-inflammatory activity of MMPP is able to be sustained, as observed in the RAW 264.7 cells.

Experimental Example 8. Analysis of Inhibitory
Effect of MMPP on NO and ROS Generation,
iNOS and COX2 Expression, and NF-κB and
STAT3 Activities in LPS- or TNF-α-Treated
Synoviocytes In Experimental Example 8, an experiment was performed to check an anti-inflammatory effect of MMPP in synoviocytes treated with LPS and TNF-α.

Figure 9:
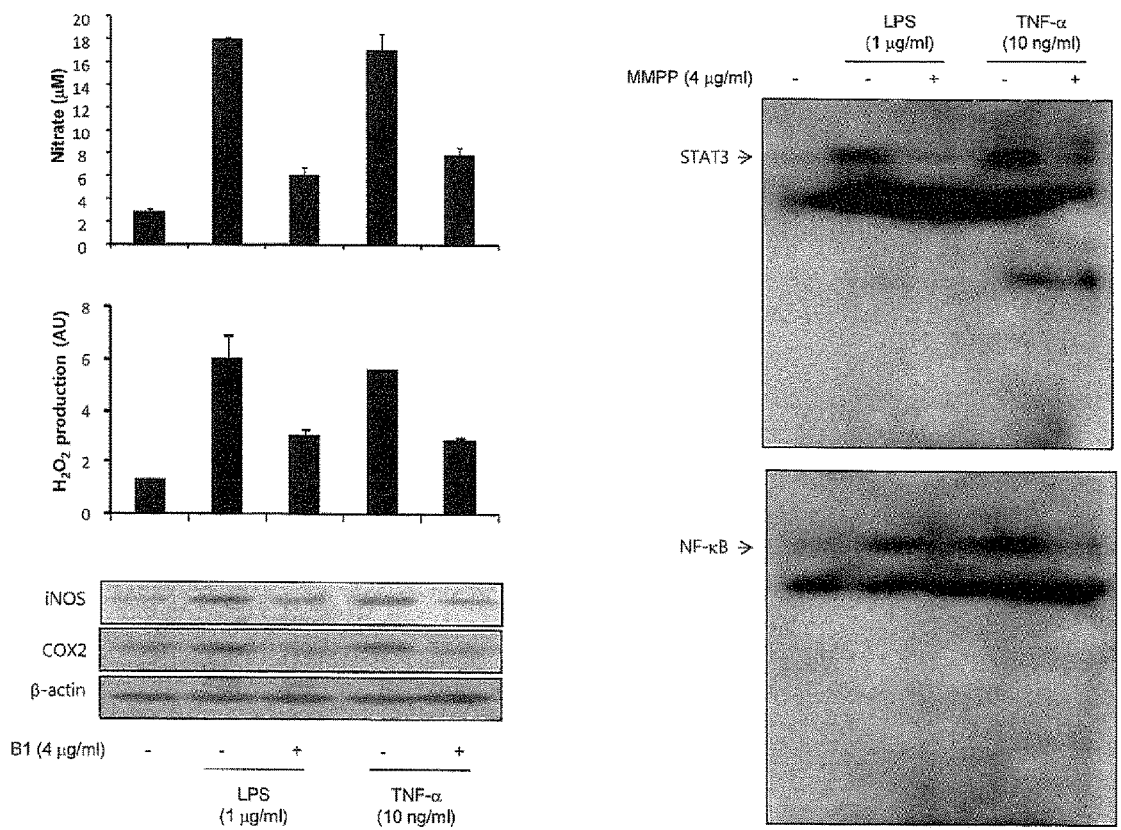
FIG. 9 shows results of Experimental Example 8: According to the presence/absence of MMPP in the presence of LPS and TNF-α, (A) is a graph plotted for results of NO and hydrogen peroxide generation, (B) is a graph and image for iNOS and COX2, (C) shows Western blotting results for STAT3 activity, and (D) shows experimental results for NF-κB activity.

It was confirmed that the LPS (1 mg/mL)- or TNF-α (10 ng/mL)-induced NO and ROS generations (FIG. 9(A)), the iNOS and COX2 expression (FIG. 9(B)), and STAT3 and NF-κB activities (FIGS. 9(C) and (D)) were reduced in the synoviocytes in the case of groups in which the RAW 264.7 cells were treated with LPS (1 mg/mL) or TNF-α (10 ng/mL) in combination with MMPP (4 mg/mL) for 24 hours.

Experimental Example 9. Analysis of
Anti-Inflammatory Effect Induced with CAIA, and
Inhibitory Effect of MMPP on Rheumatoid Arthritis
and Expression of Genes Associated with
Rheumatoid Arthritis In Experimental Example 9, it was examined whether anti-oxidative and anti-inflammatory activities of MMPP were effective for rheumatoid arthritis so that MMPP had an effect on rheumatoid arthritis. As a result, it was revealed that MMPP had an anti-arthritic effect in a collagen antibody-induced arthritis (CAIA) model.

Figure 10:
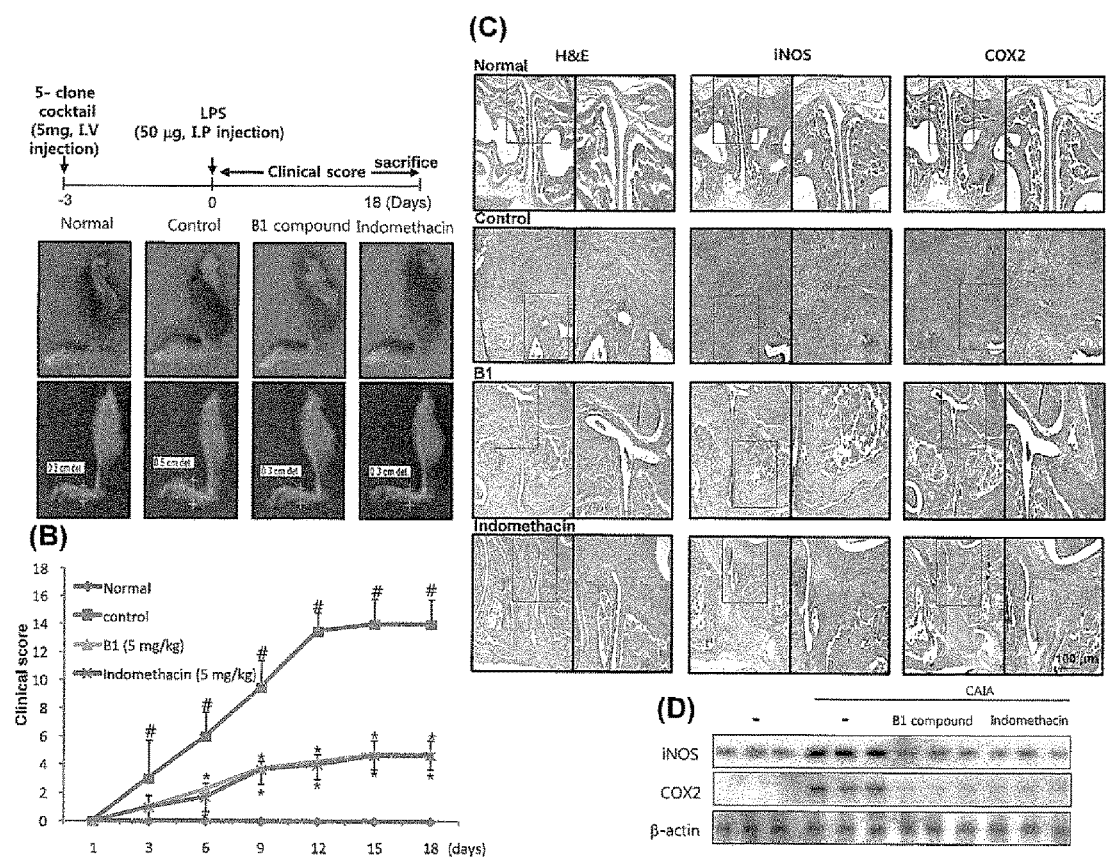
FIG. 10 shows results of Experimental Example 9: (A) is an image for clinical evaluation of ankle joints of mice, (B) shows scores for the ankle joints, (C) is a staining image of the ankle joints, and (D) is an image of iNOS and COX2.

Referring to FIG. 10(A), MMPP (5 mg/kg, p.o.) (dissolved in 100 μL of PBS including 0.5 μL of DMSO), a vehicle (a negative control), or indomethacin (5 mg/kg, p.o./dissolved in 100 mL of PBS after the dissolution) was administered daily to 7-week-old male C57BL/6 mice for 18 days. Referring to FIG. 10(B), it was revealed that a clinical score (approximately 4.67) of the group in which the mice were treated with MMPP (5 mg/kg) was 66.5% lower than a clinical score (approximately 14) of the CAIA group on the last ($18^{th}$) day. Also, it was revealed that a clinical score of the group in which the mice were treated with indomethacin (5 mg/kg) was 64.8% higher than that of the CAIA group.

When a radiographic inspection was performed on hind legs of collagen-injected mice, tissue edema and bone destruction were observed in the legs of the collagen-injected mice. However, such an effect was significantly reduced by treatment with MMPP (5 mg/kg), which was comparable to that of indomethacin (5 mg/kg) as shown in FIG. 10(B). It was confirmed through the histopathologic evaluation on ankle joints of the CAIA mice that bone destruction (pannus) and fibrosis partly occurred. On the other hand, referring to FIG. 10(C), it was revealed that the degrees of bone destruction and fibrosis were remarkably reduced in the CAIA mice treated with MMPP (5 mg/kg). Immunohistochemical and Western blotting assays were performed on affected joint tissues obtained from the CAIA mice. As a result, referring to FIGS. 10(C) and (D), it was clearly revealed that positive responses of COX2 and iNOS preferentially localized in a fibrous tissue structure around the joint.

Figure 11:
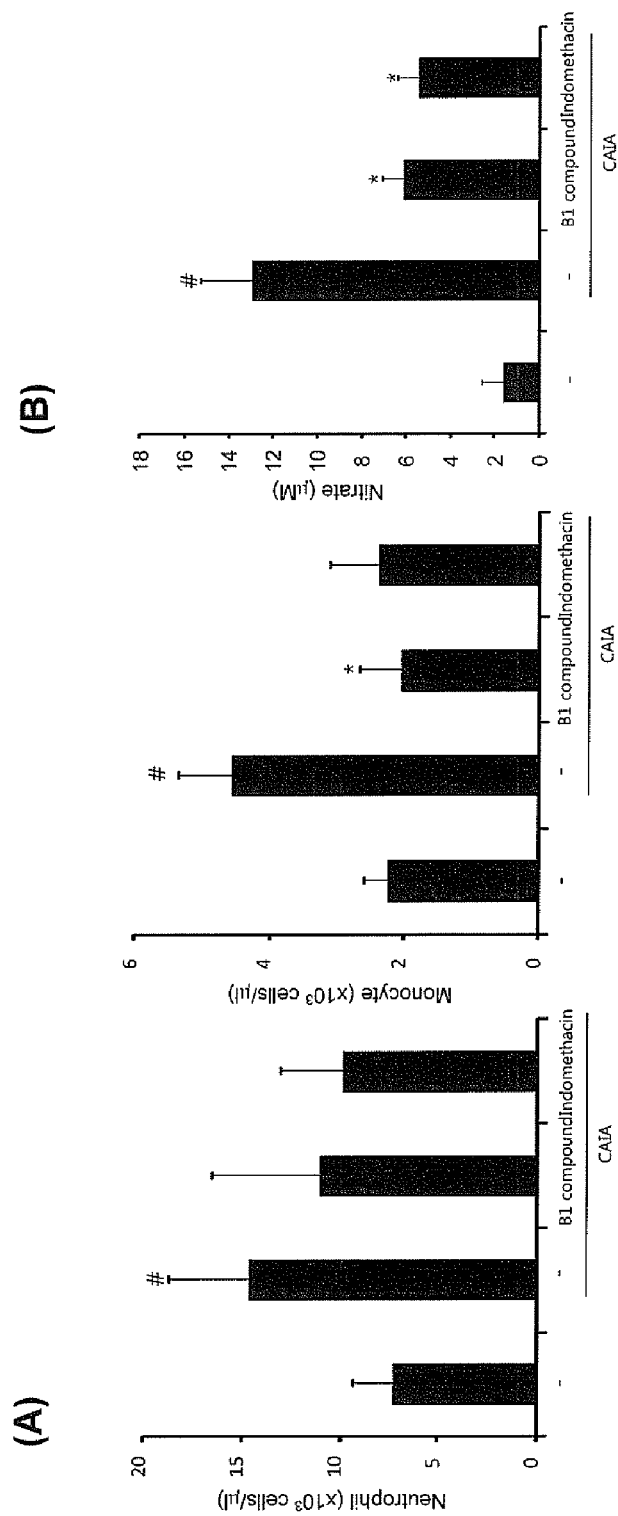
FIG. 11 shows results of Experimental Example 9: (A) to (C) are graphs illustrating STAT3 luciferase activity, hydrogen peroxide generation, and PGE2 in the presence of MMPP.

Also, it was determined whether MMPP induced a change in the number of blood cells. This is generally done to diagnose RA, monitor progression of the disease, and treat the disease. Referring to FIG. 11(A), it was revealed that the number of neutrophils and monocytes from the CAIA mice was significantly increased, compared to the control mice. Referring to FIG. 11(B), it was also revealed that the NO generation in spleen T-lymphocytes of the CAIA mice remarkably increased, compared to the control mice.

Figure 12:
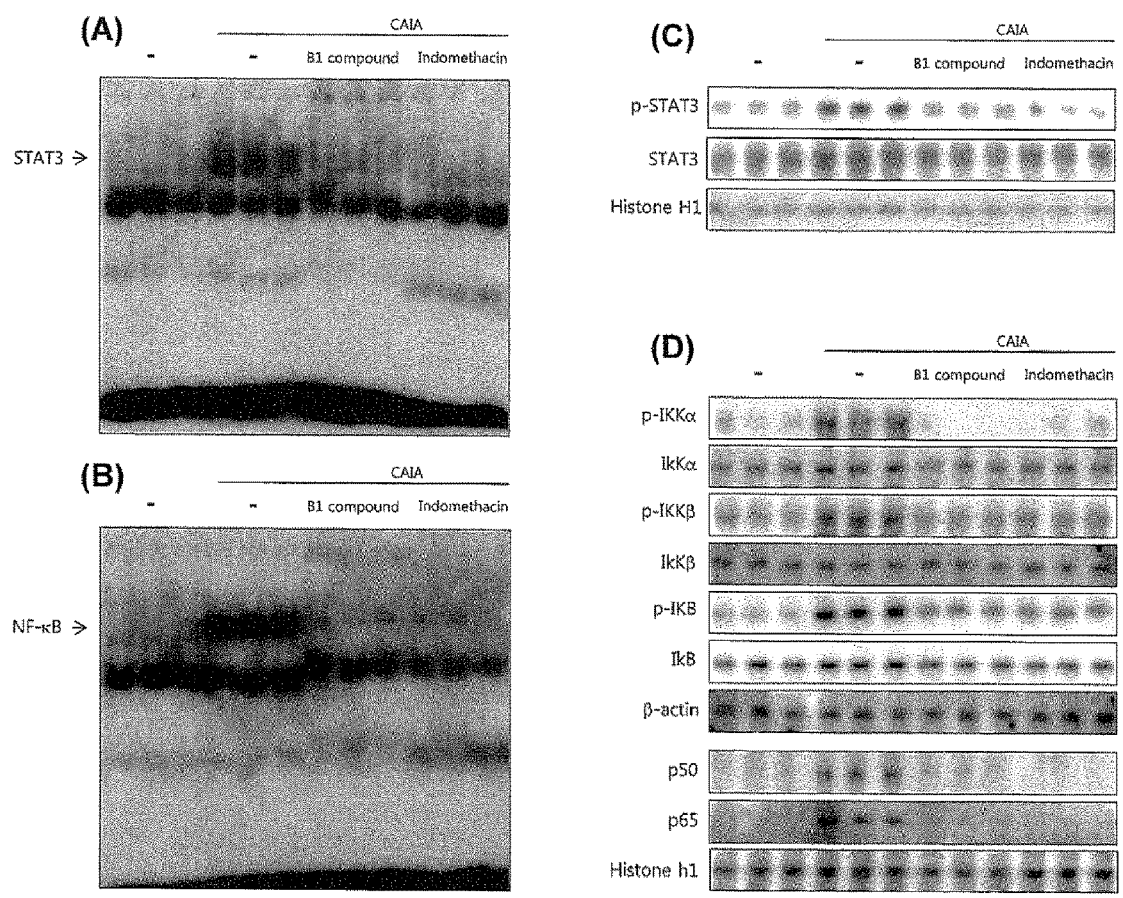
FIG. 12 shows experimental results for an inhibitory effect of MMPP on NF-κB and STAT3 in CAIA-induced C57BL/6 mice: (A) and (B) show experimental results for DNA binding activities of STAT3 and NF-κB, respectively, (C) and (D) show experimental results for STAT3, p-STAT3, p50, p65, IKK, p-IKK, IkB, and p-IkB.

In addition, the DNA binding activities of NF-κB and STAT3 were determined by EMSA. The same amount of the total proteins (20 μg/Lane) was subjected to 10% SDS-PAGE, and STAT3, P-STAT3, p50, p65, IKK, 1 KB, and p-1lkB were detected through Western blotting. A β-actin protein or histone H was used as the control. As a result, it can be seen that MMPP inhibited the STAT3 DNA-binding activity (FIG. 12(A)), the NF-κB STAT3 DNA-binding activity (FIG. 12(B)), nuclear translocation of pSTAT3, p50 and p65, and phosphorylation of IkB, IKKb and IKKa in the CAIA-induced ankle joint tissues (FIGS. 12(C) and 12(D))

Meanwhile, the compound of the present invention represented by Formula 1 may be formulated into various forms according to a purpose. Several examples of methods of preparing formulations including the compound of the present invention represented by Formula 1 as an active ingredient are described below, but the present invention is not limited thereto.

Preparation Example 1. Preparation of Powder

The following components were mixed, and the resulting mixture was then filled in an airtight pack to prepare a powder.

| | |
|---|---|
| Compound of Formula 1 | 2 g |
| Lactose | 1 g |

Preparation Example 2. Preparation of Tablet

The following components were mixed, and then tablet-pressed to prepare a tablet according to a conventional method of preparing a tablet.

| | |
|---|---|
| Compound of Formula 1 | 100 mg |
| Corn starch | 100 mg |
| Lactose | 100 mg |
| Magnesium stearate | 2 mg |

Preparation Example 3. Preparation of Capsule

The following components were mixed, and then filled in a gelatin capsule to prepare a capsule according to a conventional method of preparing a capsule.

| | |
|---|---|
| Compound of Formula 1 | 100 mg |
| Corn starch | 100 mg |
| Lactose | 100 mg |
| Magnesium stearate | 2 mg |

Preparation Example 4. Preparation of Injection

The following components were mixed, and an injection including the following components at given contents was prepared according to a conventional method of preparing an injection.

| | |
|---|---|
| Compound of Formula 1 | 100 mg |
| Mannitol | 180 mg |

-continued

| | |
|---|---|
| Na$_2$HPO$_4$•2H$_2$O | 26 mg |
| Distilled water | 2,974 mg |

INDUSTRIAL APPLICABILITY

The 2-methoxy-4-(3-(4-methoxyphenyl)prop-1-en-1-yl)phenol according to the present invention can be used to prevent or treat all types of inflammatory diseases associated with STAT3.

What is claimed is:

1. A method for treating STAT3-mediated inflammatory disease comprising administering a therapeutically effective amount of 2-methoxy-4-(3-(4-methoxyphenyl)prop-1-en-1-yl)phenol having Formula 1:

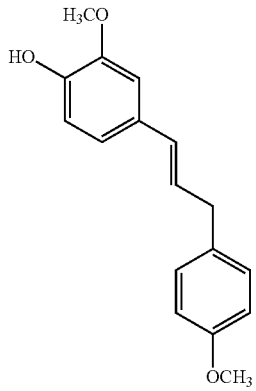 [SMILES: COc1ccc(C/C=C/c2ccc(O)c(OC)c2)cc1]

or a pharmaceutically acceptable salt thereof.

2. The method according to claim 1, wherein the STAT3-mediated inflammatory disease is selected from the group consisting of septicemia, septic shock, rheumatoid arthritis, osteoarthritis, ankylosing spondylitis, vasculitis, pleurisy, pericarditis, ischemic-related inflammation, inflammatory aneurysms, nephritis, hepatitis; chronic pulmonary inflammatory disease, bronchial inflammation, rhinitis, dermatitis, gastritis, colitis, irritable bowel syndrome, fever, myalgia caused by infection or a combination thereof.

3. The method according to claim 1, wherein the STAT3-mediated inflammatory disease comprises diseases accompanying inflammation caused by an inflammatory mediator selected from the group consisting of NO, iNOS, COX-2, PGE2, TNF-α, ikB, IL-6, and IL-1.

4. A method for treating STAT3-mediated arthritis, the method comprising administering of 2-methoxy-4-(3-(4-methoxyphenyl)prop-1-en-1-yl)phenol having Formula 1:

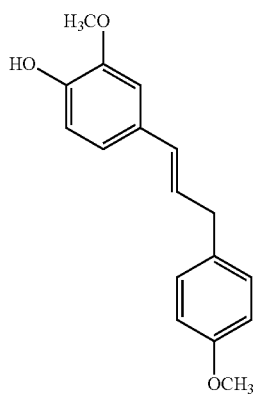

or a pharmaceutically acceptable salt thereof.

5. The method according to claim 4, wherein the STAT3-mediated arthritis comprises osteoarthritis, rheumatoid arthritis, or pyogenic arthritis.

6. The method according to claim 4, wherein the STAT3-mediated arthritis comprises diseases accompanying inflammation caused by an inflammatory mediator selected from the group consisting of NO, iNOS, COX-2, PGE2, TNF-α, ikB, IL-6, and IL-1.

* * * * *